United States Patent [19]

Gallegos

[11] Patent Number: 4,491,593
[45] Date of Patent: Jan. 1, 1985

[54] COMPOSITIONS AND METHODS FOR FERTILITY CONTROL

[76] Inventor: Alfredo J. Gallegos, 209 Calzada General Anaya, Mexico City, Mexico

[21] Appl. No.: 461,377

[22] Filed: Jan. 27, 1983

[51] Int. Cl.³ .............................................. A61K 31/19
[52] U.S. Cl. ..................................... 424/317; 424/195; 424/DIG. 12
[58] Field of Search ................................ 424/317, 195

[56] References Cited

U.S. PATENT DOCUMENTS

| | | | |
|---|---|---|---|
| 3,986,952 | 10/1976 | Kanojia et al. | 210/31 C |
| 3,996,132 | 12/1976 | Mateos et al. | 210/31 C |
| 4,006,227 | 2/1977 | Gallegos et al. | 424/195 |
| 4,046,882 | 9/1977 | Kanojia | 424/195 |
| 4,060,604 | 11/1977 | Kanojia | 424/195 |
| 4,061,739 | 12/1977 | Kanojia et al. | 424/195 |
| 4,076,805 | 2/1978 | Mateos et al. | 424/195 |
| 4,086,358 | 4/1978 | Wachter et al. | 424/278 |
| 4,112,078 | 9/1978 | Chen | 424/195 |
| 4,112,079 | 9/1978 | Chen | 424/195 |
| 4,127,651 | 11/1978 | Chen et al. | 424/195 |
| 4,130,556 | 12/1978 | Wachter et al. | 260/236.5 |

OTHER PUBLICATIONS

Martinez, Las Plantas Medicinales De Mexico, pp. 331–338, (1944).

Caballero and Walls, Productos Naturales Del Zoapatle, Bol. Inst. Quim. Univ. Nacl. Auton. Mexico, 22, 79–102, (1970).

*Primary Examiner*—Leonard Schenkman
*Attorney, Agent, or Firm*—Millard & Cox

[57] ABSTRACT

It has been found that the active principles of zoapatle are (−)-kaura-9(11),16-dien-19-oic acid, kaurenoic acid and monoginoic acid and that these acids at prescribed dosages may be used for altering the behavior of the reproductive system of a female mammal; such alterations may include inducing menses in adult female primates, synchronizing the estrous cycle in a group of mammals and preventing birth in female mammals, thus acting as a contraceptive.

25 Claims, 5 Drawing Figures

(−)-KAURA-9(11),16-DIEN-19-OIC ACID

KAURENOIC ACID

MONOGINOIC ACID

ZOAPATANOL

MONTANOL

*FIG. 5*

COMPOSITIONS AND METHODS FOR FERTILITY CONTROL

BACKGROUND OF THE INVENTION

This invention relates to methods for altering the behavior of the reproductive system of the female mammal. More specifically, the invention relates to methods for controlling fertility using substances which can be isolated from the zoapatle plant.

The name "zoapatle" is applied in Mexico to a group of plants of the family Compositae and tribe Heliantheae; the name principally designates the plant *Montanoa tomentosa* ssp. *tomentosa*, but the term is also applied to various other Montanoa species including *M. tomentosa* ssp. *microcephala* and *xanthiifolia*, *M. frutescens*, *M. leucantha* ssp. *arborescens* and *leucantha*, *M. grandiflora*, *M. speciosa* and *M. mollissima*. To the untrained eye, all these plants are similar in appearance and indeed the material sold as zoapatle leaf often turns out to be a mixture of leaves from different species. Accordingly, the term "zoapatle" will be used hereinafter to cover all of them.

It has been known for centuries that extracts of zoapatle can be used as labor inducers or to increase uterine contractions during labor, as well as to decrease post-partum bleeding. It has also been known since 1866 that such extracts can be used as menses inducers. See, inter alia, Alfaro, R., Cihopatli o Zoapatle, Gaceta Medica De Mexico, 3, 47-48 (1866); del Pozo, E., Aztec Pharmacology, Ann. Rev. Pharm. 6, 9-18 (1966); and Ortiz, de Monte Llano, B., Empirical Aztec Medicine, Science, 188, 215-220 (1975).

As with any pharmaceutical agent of natural origin, a major problem in using zoapatle extract in a controlled, scientific manner is to obtain a product of standard potency. One previous attempt to produce a product of standard potentcy is described in U.S. Pat. No. 4,006,227 granted Feb. 1, 1977 to Gallegos et al. This patent describes a composition derived from *M. tomentosa* leaves and stems by aqueous extraction with a controlled ratio of vegetable material to water at a controlled temperature. Unfortunately, even these controls are not altogether successful, since, as with many other plants, research indicates that the amount of active ingredient in Montanoa plants varies with the species, and with the conditions under which the plant is grown, including such factors as climate, humidity, soil composition and altitude. Thus, even standardizing the amount of plant material used to prepare an aqueous zoapatle extract will not result in a composition of completely reproducible properties.

Furthermore, like most natural products, the crude aqueous extract of zoapatle is known to be a very complex mixture. At least nine different compounds have been isolated from zoapatle extract and hitherto it has not been possible to identify which of these nine products is responsible for the characteristic action of the crude extract. The nine compounds involved are montanol, zoapatanol, tomentosin, montafrusin, monoginol, (−)-kaura-9(11),16-dien-19-oic acid (hereinafter sometimes referred to simply as kauradienoic acid), kaurenoic acid, zoapatlin and monoginoic acid. The structures and extraction of these compounds are described in the following papers:

Levine, S. D. et al, Zoapatanol and montanol, novel oxepane diterpenoids from the Mexican plant zoapatle (*Montanoa tomentosa*), J. Am. Chem. Soc., 101, 3404-5 (1979);

Geissman, TA, Griffin, TS, Sesquiterpene lactones, tomentosin from *Montanoma tomentosa* (cerv.), Rev. Lat. Quim., 2, 81-83 (1971);

Quijano, L. et al, Montafrusin, a new germacrolide from *Montanoa frutescens*, Phytochemistry, 18, 843-45 (1979); and Caballero, Y., Walls, F., Productos naturales del zoapatle, Bol. Inst. Quim., UNAM, 22, 79-102 (1970).

Figure 5:
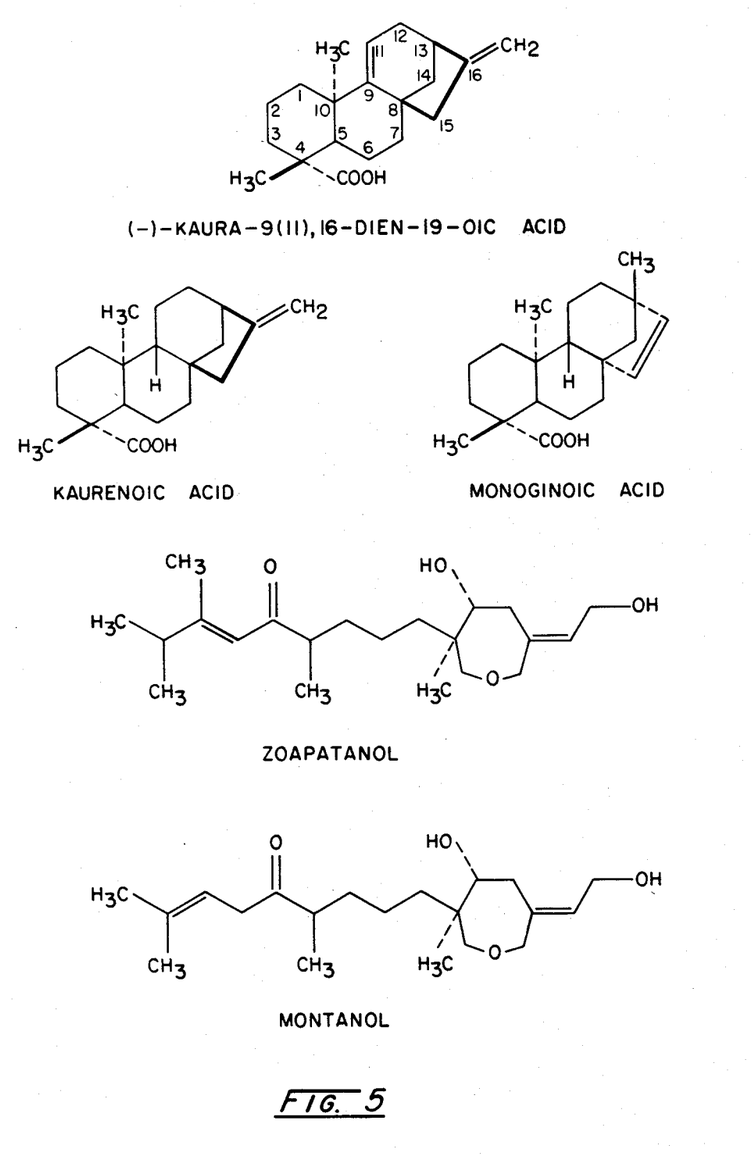
FIG. 5 shows the chemical formulae of kaurenoic acid, monoginoic acid, kauradienoic acid, zoapatanol and montanol.

The structures of kaurenoic acid, (−)-kaura-9(11),16-dien-19-oic acid, monoginoic acid, zoapatanol and montanol are also shown in FIG. 5 of the accompanying drawings. It is of course entirely possible that there are other pharmacologically active constituents of the zoapatle aqueous extract which have not yet been isolated.

For obvious reasons, faced with such a complex mixture, research workers have attempted to separate the pure compounds and to determine which one or more of them is responsible for the characteristic pharmaceutical properties of the crude extract. For example, U.S. Pat. Nos. 3,996,132, granted Dec. 7, 1976, 3,986,952, granted Oct. 19, 1976, 4,060,604, granted November 1977, 4,112,079, granted September 1978, and 4,127,651, granted November 1978, all of which are assigned to Ortho Pharmaceutical Corporation, Raritan, N.J. 08869, describe extraction and chromatographic techniques by which two pharmaceutically active compounds, now known to be the oxepane diterpenoids zoapatanol and montanol, can be extracted from the crude aqueous extract of zoapatle. In addition, the total synthesis of (±)-zoapatanol has been accomplished, as described in Nicolaou, K. C., Claremon, D. A., Barnett, W. T., Total Synthesis of (±)-zoapatanol, J. Am. Chem. Soc., 102, 6611-12 (1980). However, further research apparently indicates that neither zoapatanol nor montanol has a pharmaceutical activity corresponding to that of the crude zoapatle extract itself. For example, the aforementioned Nicolaou et al. paper states that (±)-zoapatanol in vitro shows constriction of the cat coronary artery and contraction of isolated guinea-pig ileum, but fails to contract the non-pregnant rabbit and rat uterus, whereas the crude zoapatle extract elicits a clear a reproducible response upon the uterine contractility of the non-pregnant rabbit and vascular relaxation, without altering intestinal peristalsism, in rabbits, guinea-pigs, monkeys and humans.

Not only has the search for the "active principle" of crude zoapatle extract been hindered by the complexity of the mixtures and the difficulty of isolation of pure compounds therefrom, it has also been bedevilled by the lack of consistency in the results achieved with varying animal models. Because of the length, cost, and complexity of in vivo evaluation of zoapatle-derived compounds, it is necessary to test biological activity in vitro. Unfortunately, hitherto there has been no systematic attempt to investigate the appropriateness of various animal models and their correlation with the known effects in primates. As a result, the literature is filled with a great number of biological observations showing apparently contradictory or conflicting results. For example, the aforementioned Caballero et al. paper reports that monoginoic and kaurenoic acids isolated from zoapatle roots showed a complete lack of in vitro activity. These results were based upon experiments with isolated rat uterine strips and observations that these two acids failed to increase the tone or frequency of the contractions of such isolated rat uterine strips. It is now known that rat uterine strips do not increase tone or frequency of contractions when exposed to crude zoapatle extract and in fact display the opposite effect of relaxation. On the other hand, we have found that the effect of zoapatle-derived compounds on isolated strips of guinea pig uterus does correlate correctly with the activity of such compounds in female mammals.

There is thus a need for identification of the active principle of zoapatle. We have now identified this active principle.

BRIEF DESCRIPTION OF THE INVENTION

I have discovered that the principal uterotonically active compounds of zoapatle are kaurenoic acid, monoginoic acid and kauradienoic acid, and thus that, these acids may be used for any of the purposes for which crude zoapatle extracts have hitherto been used, as described for example in the aforementioned U.S. Pat. No. 4,006,227.

Accordingly, the invention provides a method of altering the behavior of the reproductive system in a female mammal which comprises administering internally to the female mammal, in an amount of from about 0.1 to about 10 mg/kg. body weight, a kaurenoic acid compound selected from the group consisting of kaurenoic acid, monoginoic acid and (−)-kaura-9(11),16-dien-19-oic acid.

The invention also provides a method of altering the behavior of the reproductive system of a female mammal which comprises administering internally to the female mammal a kaurenoic acid compound selected from the group consisting of kaurenoic acid, monoginoic acid and (−)-kaura-9(11),16-dien-19-oic acid, the kaurenoic acid compound being substantially free of zoapatanol and/or montanol.

DETAILED DESCRIPTION OF THE INVENTION

As stated above, the instant invention is based upon the discovery that the active principles of zoapatle are kaurenoic acid, monoginoic acid and kauradienoic acid. In practicing the instant invention, any of these three compounds may be used alone or in admixture, but the preferred compound for use in the instant invention is kaurenoic acid.

The alterations in the behavior of the female mammalian reproductive system which can be effected by the instant methods include all such alterations which have hitherto been effected by the crude zoapatle extract. Such alterations include the use of the kaurenoic acid compounds to induce menses in adult female primates. Although this method may simply be used for the regulation of menstruation when difficulties are occuring, such as in cases of amenorrhea, it will of course normally be used where the female is pregnant and the kaurenoic acid compound is administered in sufficient amounts to terminate pregnancy. Thus, the kaurenoic acid compound functions as an anti-fertility agent.

The instant methods may also be used to synchronize the birth of young to a group of animals such as sheep and cattle. For this purpose, the kaurenoic acid compound is administered to a group of female mammals as a progesterone-regulating composition to prevent conception. The members of the group are allowed to become fertile within a short time period, at least some of the members are rendered pregnant during this time period, and thereafter young are delivered at or near term in a biologically synchronized time span. This method of synchronizing the birth of young, which depends upon the use of the kaurenoic acid compound as a progesterone-regulating composition to synchronize the estrous cycle in a group of mammals, has substantial economic value. Sheep flocks, cattle herds or other groups of mammals can be subjected to biological synchronization to control the time span during which births occur if the females can be controlled in their fertility at the beginning of seasonal fertilization cycles. Such synchronization of the estrous cycle can enable more than a single offspring to be produced per female in a herd within a one-year period; in some species there could be two or more deliveries a year. Also, such biological synchronization can result in great efficiencies in delivering an entire flock of offspring within a relatively short time span, such as a few days, rather than allowing them to occur naturally over a period of several weeks, thereby greatly reducing the time within which a herdsman and/or a veterinarian must attend the flock in order to supervise deliveries.

A third type of alteration of the behavior of the reproductive system of a female mammal which can be effected by the instant methods is preventing birth in female mammals by administration of the kaurenoic acid post-coitally. For this purpose, the kaurenoic acid compound may be administered into the uterus of the female mammal, but for obvious reasons of reducing risk, is preferably administered orally. When used for preventing birth, the kaurenoic acid compound is desirably administered during the luteal phase of a menstrual cycle.

As already mentioned, in the first instant method, the kaurenoic acid compound is administered internally to the female mammal in an amount of from about 0.1 to about 10 mg/kg. body weight of the female mammal. The preferred amount of the female mammal. The preferred amount of kaurenoic acid compound is from about 0.3 to about 3 mg/kg. Possible routes for administration include subcutaneous, intramuscular, intravenous, intrauterine and oral routes, the oral route usually being the most convenient.

In the instant methods, the kauenoic acid compounds (kaurenoic acid itself, monoginoic acid and (−)-kaura-9(11),16-dien-19-oic acid) can be used in a variety of forms. The kaurenoic acid compounds are preferably used in substantially pure form, in order to avoid any possible complications resulting from admixed, physiologically-active compounds. In view of the known physiological activity of zoapatanol, it is particularly desirable that the kaurenoic acid compound be free from zoapatanol, and we also prefer that the kaurenoic acid compound be free from montanol. Indeed, it is preferred that the kaurenoic acid compound used in the instant method be free from all zoapatle-derived compounds other than the kaurenoic acid compounds themselves. However, the instant methods do not exclude the possibility that the kaurenoic acid compounds are used in the form of mixtures with other zoapatle-derived compounds. Indeed, (although this is not recommended) the first instant method extends to the use of the crude aqueous extract of zoapatle, provided that this aqueous extract is standardized so as to provide to the female mammal the kaurenoic acid compound in an amount within the aforementioned ranges.

Kauradienoic acid is a known compound and its isolation and characterization from *M. tomentosa* roots are described in the aforementioned paper by Caballero et al. Although I prefer to use kauradienoic acid isolated from zoapatle leaves by the technique described below, because the zoapatle plant is known to be free of toxic substances, the invention is not restricted to kauradienoic acid prepared by any particular technique, and the acid may be extracted from plants other than zoapatle as described for example in Cannon, J. R. et al, Isolation of (−)-Kaura-16-dien-19-oic acid and 15 β-hydroxy-(−)-1-kaura-16-en-19-oic acid from Phebalium rude, Aust. J. Chem., 19, 861 (1966) and Kloss, P., Arch. Pharm. (Weinheim), 302, 376 (1969) Chem. Abstr., 71, 57535, (1969) and Brieskorn, C. H. et al, Tetrahedron, 5661 (1968), Chem. Ber., 102, 2621 (1969). (The Kloss and Brieskorn papers describe the extraction of kauradienoic acid from *Espeletia schultzii*, but do not use the term "kauradienoic acid"; Kloss designates the compound as "grandiflorenic acid", while Brieskorn terms the compound "Sl acid". The identification of these preparations as kauradienoic acid is reported in Piozzi, F. et al, Can. J. Chem. 50, 109 (1972). An earlier Piozzi et al paper in Gazz. Chim. Ital., 98, 907 (1968) describes the extraction of kauradienoic acid (the compound is named as grandiflorenic acid) from *Espeletia grandiflora*.)

Figure 1:
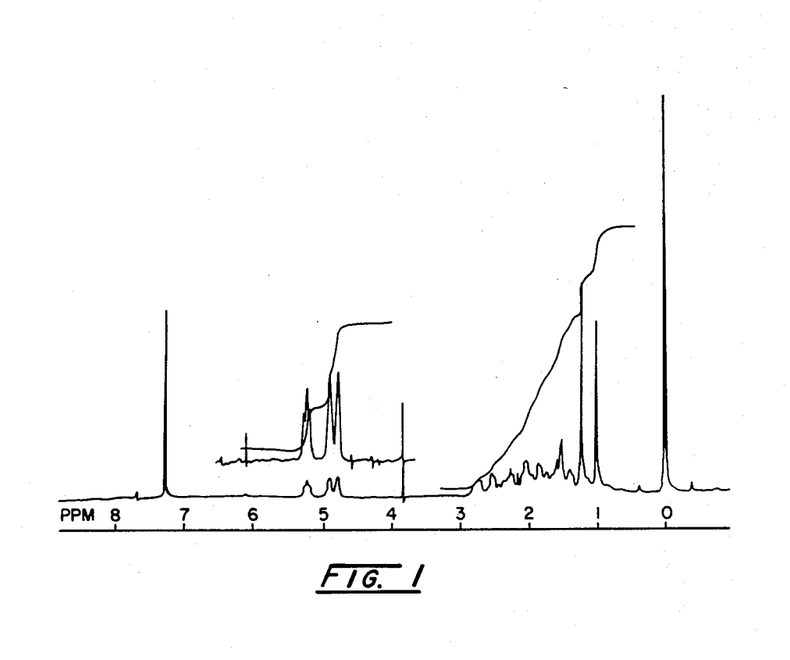
FIG. 1 shows the proton magnetic resonance spectrum of kauradienoic acid.

The presently preferred technique for extracting kauradienoic acid from zoapatle is similar to that described in the aforementioned paper by Caballero et al. In this presently preferred method, dried leaves of the Montanoa plant are extracted with a hydrocarbon solvent, preferably hexane, and the resultant hydrocarbon extract is evaporated under reduced pressure to remove a major portion of the hydrocarbon solvent and leave a syrupy residue. This syrupy residue is chromatographed on silica gel with a hexane:ethyl acetate eluant and the appropriate fractions containing the kauradienoic acid (which may be detected by routine spectral tests, including the detection of its proton NMR spectrum shown in FIG. 1) are re-chromatographed after removal of solvent and evaporated to dryness under reduced pressure to yield a powder. This powder is preferably then recrystallized from a mixture of petroleum and diethyl ethers to yield pure kauradienoic acid.

The Montanoa species used in this extraction procedure is desirably *M. tomentosa*, most desirably the subspecies *tomentosa*. Desirably, the Montanoa leaves are dried prior to the extraction with the hydrocarbon solvent, which is preferably hexane. It should be noted that all parts of the Montanoa plant contain kauradienoic acid and this acid can be extracted from parts of the plant other than the leaves; for example, useful amounts of kauradienoic acid can be extracted from Montanoa roots as explained in the aforementioned paper by Caballero et al. However, in order to avoid injury or killing of plants, it is preferred to extract the kauradienoic acid from the leaves of the plant.

It may appear surprising that a hydrocarbon solvent is used for the initial extraction of kauradienoic acid from Montanoa leaves, since kauradienoic acid is present in the crude aqueous extract prepared by boiling the leaves with water. However, kauradienoic acid itself is more soluble in hydrocarbon solvents than in aqueous solvents. It appears that in the Montanoa leaves kauradienoic acid is linked to sugars which confer water-solubility on the acid but that during the extraction process the acid is separated from the accompanying sugars so that the acid is extracted by the hydrocarbon solvent.

Kaurenoic acid and monoginoic acid may be extracted from Montanoa plants by the methods described in the aforementioned paper by Caballero et al. Naturally, any of the three kaurenoic acid compounds prepared synthetically could be used if desired, although at present no synthetic routes to these compounds appear to be described in the literature.

It should be noted that the crude hexane extract prepared in the first stage of the presently preferred technique for extracting kauradienoic acid from zoapatle leaves contains kaurenoic acid and monoginoic acid in addition to the kauradienoic acid, and may thus be used for the preparation of all three of the kaurenoic acid compounds. Separation of the three compounds may be effected by chromatography using as the solid phase octadecylsilane bonded to 10 μm.silica (available commercially under the trade name Micropak MCH-10 from Varian Instruments) and using a liquid phase comprising an 80% acetonitrile/20% water v/v mixture. For example, we have used the aforementioned solid phase in a 30 cm. by 4 mm. stainless steel column operating at 50° C. and at a rate of 1 ml/min., a pressure of 78 atmospheres being reached under these conditions. Using this chromatography technique, kauradienoic acid eluted after approximately 5 minutes, kaurenoic acid after approximately 6 minutes 20 seconds and monoginoic acid after approximately 7 minutes.

The presently preferred method for the extraction of kauradienoic acid is described below, together with in vitro and in vivo tests on the resultant product, and in vivo tests on kaurenoic acid and monoginoic acid, will now be described, though by way of illustration only.

EXTRACTION OF KAURADIENOIC ACID

Leaves of *Montanoa tomentosa* were gathered, dried, ground to a fine powder and stored in glass jars protected from direct light. To extract kauradienoic acid from these dried leaves, 1.3 kg. of the dried leaves were extracted three times with 3.5 l. aliquots of hexane, the dried leaves simply being allowed to stand in each aliquot of hexane for 48 hours at room temperature, then the residual solid material was filtered from the hexane extract. The three hexane extracts were combined and evaporated under reduced pressure to yield 78 g. of a syrupy crude material. 10 g. aliquots of this crude material were chromatographed on a 70–230 mesh silica gel column previously deactivated with water in an amount of 8% w/w. The silica gel column was then eluted with a 7:3 v/v hexane:ethyl acetate mixture. Fractions of approximately 125 ml. were collected and fractions 17–24, which were found to contain the kauradienoic acid, were rechromatographed after removal of solvent and evaporated to dryness under reduced pressure to yield a powder having a melting point of 156°–158° C. This powder was recrystallized from a mixture of petroleum and diethyl ethers to yield pure kauradienoic acid, which was characterized by means of its ultraviolet, infrared, mass and proton magnetic resonance spectra. The proton magnetic resonance spectrum of the product is reproduced in FIG. 1, and this spectrum clearly shows that the product is entirely different from those described in the aforementioned U.S. Pat. Nos. 3,986,952 and 3,996,132. The mass spectrum is reproduced in the aforementioned paper by Caballero et al.

For use as controls in the animal experiments described below, two other extracts of zoapatle were prepared. The first, zoapatle aqueous crude extract (hereinafter referred to as ZACE) was a standardized aqueous extract prepared in accordance with the aforementioned U.S. Pat. No. 4,006,227 by boiling 10.0 g. of the dried leaves in 100 ml. of distilled water for 10 minutes, then filtering through a Whatman #1 filter paper. In all cases this product was used immediately after preparation. The second control extract, hexane extract (hereinafter sometimes referred to as HE) was prepared by dissolving 5 mg. of the crude syrupy material obtained by evaporation of the hexane extract in a 1:1 v/v acetone:methanol mixture, adding distilled water and evaporating under reduced pressure to remove the organic solvents. The final volume of the resultant aqeous suspension of the crude hexane extract was adjusted to 5 ml. with distilled water. An exactly similar procedure was used to prepare an aqueous suspension of kauradienoic acid for use in the biological tests described below.

BIOLOGICAL TESTS

The effects of kauradienoic acid, zoapatle aqueous crude extract and hexane extract were evaluated on isolated rat and guinea-pig uterine strips and on the uterine contractility of guinea-pigs in vivo. The rats used were pregant and non-pregnant Wistar rats weighing 200–250 g. and pregnant and non-pregnant female adult guinea-pigs of the Hardly strain weighing 450–500 g. each. In the case of the non-pregnant guinea-pigs, only those in diestrous were used, their hormonal state being established by daily vaginal smears. In the experiments using isolated uterine strips, each animal was treated with 10 micrograms of estradiol benzoate subcutaneously, 48 and 24 hours prior to sacrifice. The animals were sacrificed by a blow to the neck and immediately both uterine horns were dissected out and placed in a petri dish containing a modified Ringer solution containing the following numbers of milimoles of various salts: NaCl 154: KCl 5: $CaCl_2$ 0.8: $MgCl_2$ 0.12: $NaHCO_3$ 5.9; glucose 2.5. This solution was adjusted to pH 7.4 with a 5% carbon dioxide: 95% oxygen gas mixture and maintained at a constant temperature of 37±1° C. by means of a water bath. Each of the uterine horns was divided into three segments each measuring approximately 1 cm. in length.

The contractility of the uterine strips was isometrically recorded using a tension transducer connected to a polygraph. For this purpose, immediately after the cutting of the strips, the strips were immediately placed in an incubation chamber containing 5 ml. of the aforementioned modified Ringer solution; one end of the segment was fixed to the floor of the chamber and the other to a model FTO 3 tension transducer connected to a model 7B Grass polygraph. Once the spontaneous contractility of the uterine strips had been recorded, the ZACE, HE and kauradienoic acid test samples were separately added directly to the incubation chamber and the effect produced on the uterine contractility was recorded for ten minutes. After these observations were terminated, the uterine strips were washed several times with the aforementioned modified Ringer solution to remove the active material and new observations were not performed until the spontaneous contractility of the uterine strips returned to the control value recorded prior to the start of the experiments.

For the in vivo recordings of uterine contractility, adult female guinea-pigs of approximately 450 g. body weight were anesthetized with 25 mg/kg. of sodium pentobarbital administered subcutaneously. Following surgical exposure of the uterus, an elastic catheter was introduced through the vagina into the uterus and a small spherical rubber globe at the tip of the catheter was settled in the middle portion of one of the uterine horns. The catheter was then filled with approximately 0.3 ml. of water and connected to a pressure transducer, the output from which was supplied to a three-channel polygraph. The catheter was fixed to the abdominal wall and the incision sutured closed. The arterial blood pressure of the animal was recorded with the aid of a catheter introduced into the left carotid artery and connected to a pressure transducer, while electrocardiographic recordings were obtained from skin electrodes arranged in a V4 pattern. A catheter was placed in the radial vein to allow intraveneous administration of the test materials.

Figure 2:
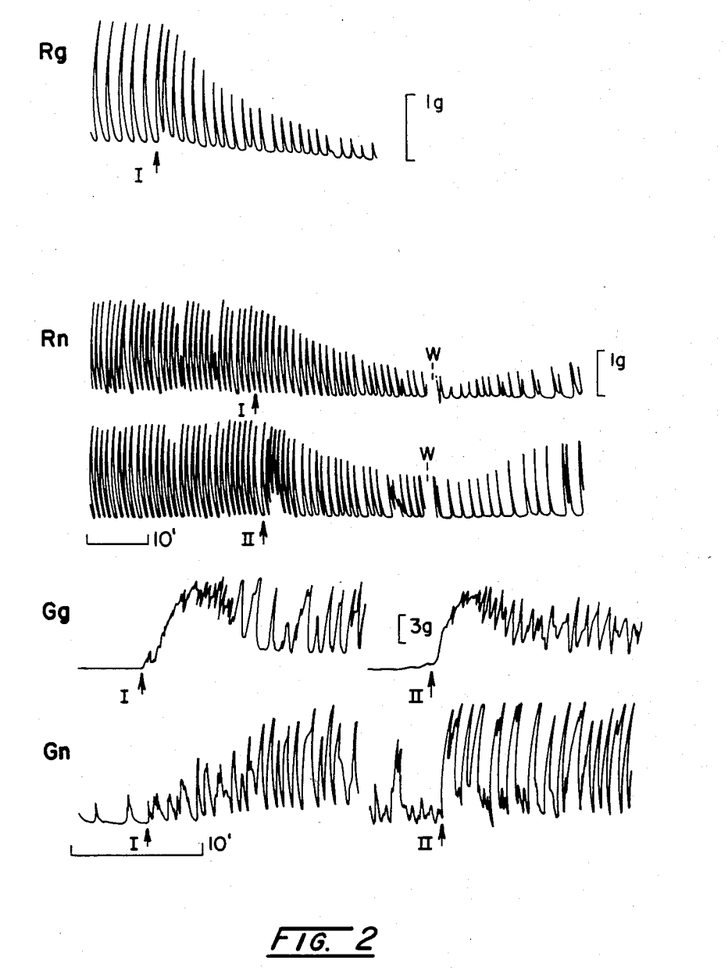
FIG. 2 shows the effects produced by crude aqueous zoapatle extract and the crude hexane extract on isolated rat and guinea-pig uterine strips.

The results obtained using ZACE and HE on isolated rat and guinea-pig uterine strips are shown in FIG. 2, wherein the designation $R_g$ denotes results obtained from pregnant rat strips, $R_n$ designates results obtained from non-pregnant rat strips, $G_g$ designates results obtained from a pregnant guinea-pig and $G_n$ denotes results obtained from a non-pregnant guinea-pig. The curves designated I were obtained by adding 20 μl/ml. of ZACE to the incubation chamber, while the curves designated II were obtained by adding 40 μl/ml. of HE to the incubation chambers. The point of introduction of the test material into the incubation chambers is indicated by the arrow below each curve.

It will be seen from FIG. 2 that both ZACE and HE caused a gradual decrease in the amplitude of the spontaneous uterine contractility in the non-pregnant rat uterine strips ZACE acted similarly on the pregnant rat strips. On the other hand, both ZACE and HE elicited an immediate increase in the uterine contractility of both pregnant and non-pregnant guinea-pigs. In all cases, repeated washing of the uterine strips with the aforementioned modified Ringer solution restored the uterine contractility to its control value, but only after an extended period.

The results presented in FIG. 2 show that the crude hexane extract of zoapatle does indeed contain the active principle thereof, as shown by the close similarity between the curves obtained using ZACE and HE. Furthermore, the results presented in FIG. 2 show that isolated rat uterine strips are not a suitable model for testing the activity of ZACE components for their activity in female primates, since the action of ZACE on rat uterine strips is totally different from that observed in female primates. The isolated guinea-pig uterine strip is a much more suitable model.

Figure 3:
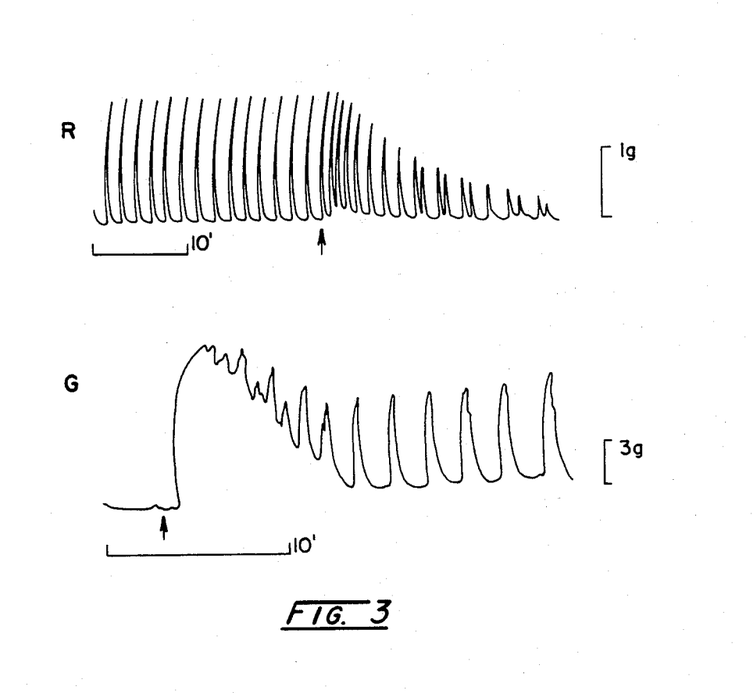
FIG. 3 shows the effect produced by kauradienoic acid on isolated rat and guinea-pig uterine strips.

FIG. 3 shows the results obtained by adding 20 μl/ml. of pure kauradienoic acid, isolated by the technique described above, to isolated uterine strips of rat and guinea-pigs; the curve designated R was obtained from a pregnant rat strip and the curve designated G from a pregnant guinea-pig strip. As in FIG. 2, the point of addition of the test material into the incubation chamber is indicated by an arrow. It will be seen that in both cases the results obtained with kauradienoic acid are closely similar to those obtained with ZACE and with HE, thus confirming that kauradienoic acid is the principle active component responsible for the effects of the crude aqueous extract and the hexane extract on uterine tissue. Similar results are obtained using kaurenoic acid.

Figure 4:
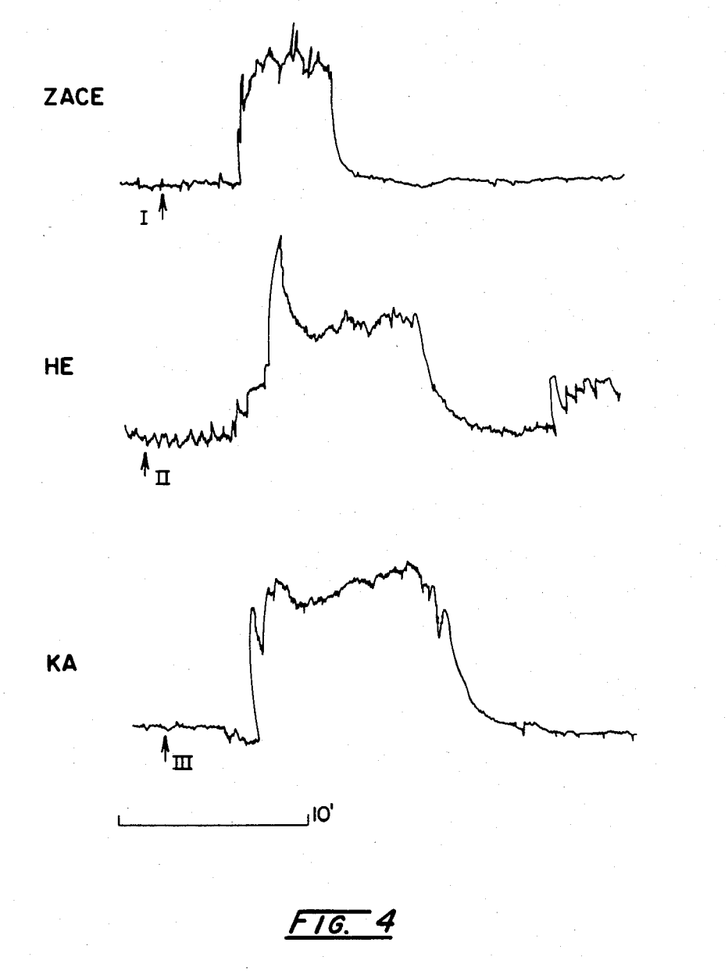
FIG. 4 shows the effects induced by crude zoapatle extract, hexane extract and kauradienoic acid on the uterine contractility of guinea-pigs in vivo.

FIG. 4 shows the effects induced by ZACE, HE and kauradienoic acid on the unterine contractility of guinea-pigs in vivo. Curve I in FIG. 4 was obtained using 90 µl. of ZACE intraveneously, Curve II using 180 µg. of HE intraveneously and Curve III using 90 µg. of kauradienoic acid. As in FIGS. 2 and 3, the point of injection of the test material is marked by an arrow. The spontaneous uterine contractility of the guinea-pig in vivo is of low amplitude and the pressure changes recorded are partially due to respiratory movements causing changes in the pressure within the abdominal cavity. Four minutes after the intraveneous injection of the ZACE, strong tonic uterine contractility was observed lasting for 5–7 minutes. No significant changes in arterial blood pressure, cardiac activity or intestinal peristalsis were observed. Similar effects are observed after administration of HE or kauradienoic acid, but the utertonic effect is of longer duration and higher intensity when HE or kauradienoic acid are used.

It will be seen from a comparison of the three curves in FIG. 4 that the shape of the curve obtained using the pure kauradienoic acid more closely resembles that obtained using ZACE than that obtained using the hexane extract, the hexane extract tending to produce a very sharp initial increase in pressure. In as much as this sharp initial increase in pressure is likely to be undesirable in most applications, these results would appear to indicate that the use of pure kauradienoic acid is preferable to the use of the hexane extract.

In a further series of tests, pure kaurenoic acid, obtained in the manner described above was administered to pregnant female rats. At a dosage of 272 µg. per rat, the kauradienoic acid produced 100% resorbtion of all fetuses. Similar results were obtained using kauradienoic acid and monoginoic acid.

Further tests conducted upon zoapatanol and montanol have shown that these compounds are not responsible for the characteristic effects of zoapatle crude aqueous extract.

It will be apparent to those skilled in the art that numerous changes and modifications can be made in the embodiments of the invention already described without departing from the scope of the invention. Accordingly, the foregoing description is to be construed in an illustrative and not in a limitative sense, the scope of the invention being defined solely by the appended claims.

I claim:

1. A method of effecting an alteration in the reproductive system of a female mammal which comprises administering internally to said female mammal a pharmaceutical composition which is substantially free of zoapatanol and which comprises a kaurenoic acid compound selected from the group consisting of kaurenoic acid and (−)-kaura-9(11), 16-dien-19-oic acid, the amount of said kaurenoic acid compound administered being from about 0.1 to about 10 mg/kg. body weight of said female mammal, and said alteration in the behavior of said reproductive system being selected from the group consisting of:

(a) induction of a mensis (b) administration of said pharmaceutical composition to a group of female mammals to initially prevent pregnancy, allowing the members of said group to become fertile within a short time period, rendering at least some of said members pregnant during said time period, and thereafter delivering young at or near term in a biologically synchronized time span; and (c) prevention of birth by administration of said pharmaceutical composition post-coitally to said female mammal.

2. A method according to claim 1 wherein said alteration in the behavior of said reproductive system comprises the induction of a mensis.

3. A method according to claim 2 wherein said female is pregnant and said pharmaceutical composition is administered to said female in sufficient amounts to terminate pregnancy.

4. A method according to claim 1 wherein said pharmaceutical composition is administered to a group of female mammals to prevent pregnancy, the members of said group are allowed to become fertile within a short time period, at least some of said members are rendered pregnant during said time period, and thereafter young are delivered at or near term in a biologically synchronized time span.

5. The method of claim 4 wherein the group of mammals is a flock of sheep.

6. The method of claim 4 wherein the group consists of cattle.

7. The method according to claim 1 wherein said pharmaceutical composition is administered post-coitally to said female mammal to prevent birth.

8. A method according to claim 7 wherein said pharmaceutical composition is administered during the luteal phase of a menstrual cycle of a primate.

9. A method according to claim 1 wherein said pharmaceutical composition is administered into the uterus of said female mammal.

10. A method according to claim 1 wherein said pharmaceutical composition is administered orally to said female mammal.

11. A method according to claim 1 wherein said pharmaceutical composition comprises substantially pure kaurenoic acid.

12. A method according to claim 11 wherein said kaurenoic acid is administered to said female mammal in an amount of about 0.3 to about 3 mg/kg. body weight.

13. A method according to claim 1 wherein said pharmaceutical composition is substantially free of zoapatle-derived compounds other than said kaurenoic acid and (−)-kaura-9(11), 16-dien-19-oic acid.

14. A method of effecting an alteration in the behavior of the reproductive system of a female mammal which comprises administering internally to said female mammal a pharmaceutical composition which is substantially free of montanol and which comprises a kaurenoic acid compound selected from the group consisting of kaurenoic acid and (−)-kaura-9(11), 16-dien-19-oic acid, the amount of said kaurenoic acid compound administered being from about 0.1 to about 10 mg/kg. body weight of said female mammal, and said alteration in the behavior of said reproductive system being selected from a group consisting of:

(a) induction of a mensis;

(b) administration of said pharmaceutical composition to a group of female mammals to initially prevent pregnancy, allowing the members of said group to become fertile within a short time period, rendering at least some of said members pregnant during said time period, and thereafter delivering young at or near term in a biologically synchronized time span; and (c) prevention of birth by administration of said pharmaceutical composition post-coitally to said female mammal.

15. A method according to claim 14 wherein said alteration in the behavior of said reproductive system comprises the induction of a mensis.

16. A method according to claim 15 wherein said female is pregnant and said pharmaceutical composition is administered to said female in sufficient amounts to terminate pregnancy.

17. A method according to claim 14 wherein said pharmaceutical composition is administered to a group of female mammals to prevent pregnancy, the members of said group are allowed to become fertile within a short time period, at least some of said members are rendered pregnant during said time period and thereafter young are delivered at or near term in a biologically synchronized time span.

18. The method of claim 17 wherein the group of mammals is a flock of sheep.

19. The method of claim 17 wherein the group consists of cattle.

20. A method according to claim 14 wherein said pharmaceutical composition is administered post-coitally to said female mammal to prevent birth.

21. A method according to claim 20 wherein said pharmaceutical composition is administered during the luteal phase of a menstrual cycle of a primate.

22. A method according to claim 14 wherein said pharmaceutical composition is administered into the uterus of said female mammal.

23. A method according to claim 14 wherein said pharmaceutical composition is administered orally to said female mammal.

24. A method according to claim 14 wherein said pharmaceutical composition is also substantially free of zoapatanol.

25. A method according to claim 14 wherein said pharmaceutical copmosition is administered in an amount sufficient to provide said kaurenoic acid compound in an amount from about 0.3 to about 3 mg/kg. body weight of said female mammal.

* * * * *